July 26, 1960 H. A. M. VERSCHUREN Plant Pat. 1,961
ROSE PLANT
Filed Oct. 16, 1959
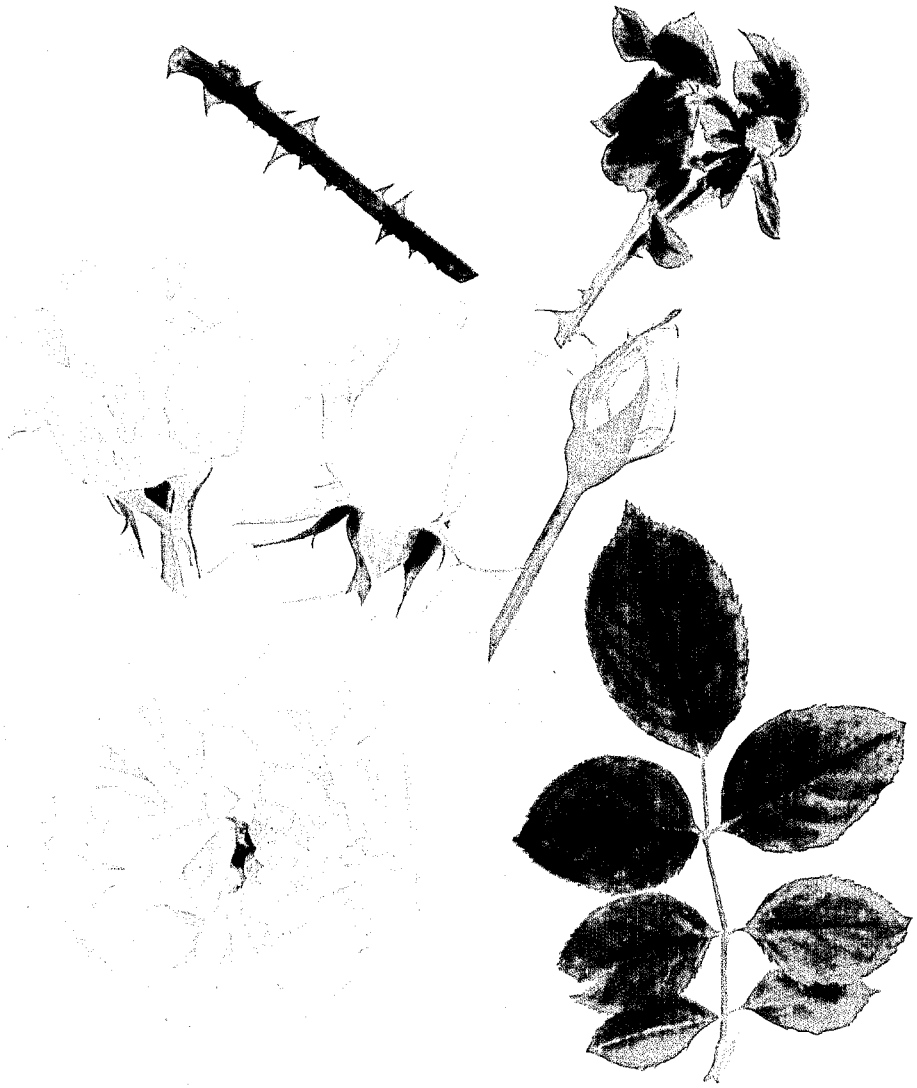
Inventor.
H. A. M. Verschuren
By: Robb & Robb
Attorneys.

United States Patent Office

Plant Pat. 1,961
Patented July 26, 1960

1,961

ROSE PLANT

Hendrikus Antonie Maria Verschuren, Haps, Netherlands, assignor to Jackson & Perkins Company, Newark, N.Y., a corporation of New York Filed Oct. 16, 1959, Ser. No. 847,034

1 Claim. (Cl. 47—61)

The present invention relates to a new and distinct variety of rose plant of the hybrid tea class, which was originated by me by crossing the variety "Orange Delight" (U.S. Plant Patent No. 874) with the variety "Golden Rapture" (unpatented).

The primary objective of this breeding was to produce a new rose variety having the deep flower color of the parent variety "Orange Delight," but combined with greater flower productivity than normally prevails in the case of this parent, and still further combined with a suitability for cut-flower use. This objective was fully achieved, along with other desirable improvements, as evidenced by the following unique combination of characteristics which are outstanding in the new variety and which distinguish it from its parents, as well as from all other varieties of which I am aware:

(1) A free blooming habit which is especially desirable for cut-flower purposes, with attendant suitability for greenhouse cut-flower production;

(2) Strong flower stems, which are unusual in a rose of this color;

(3) A distinctive Capucine Buff, lightly overcast with Orange-Pink general color tonality of the flowers; and (4) Substantially uniform retention of the flower color from beginning to end.

Asexual reproduction of the new variety by budding, as performed at Newark, New York, U.S.A., and also at Pleasanton, California, U.S.A., shows that the foregoing characteristics and distinctions come true to form and are established and transmitted through succeeding propagations.

The accompanying drawing shows typical specimens of the vegetative growth and flowers of my new variety in different stages of development and is depicted in color as nearly true as it is reasonably possible to make the same in a color illustration of this character.

The following is a detailed description of the new variety, with color terminology in accordance with Ridgway's Color Standards and Nomenclature:

Parentage: Seedling.
*Seed parent.*—"Orange Delight."
*Pollen parent.*—"Gold Rapture."
Classification:
*Botanic.*—Hybrid tea.
*Commercial.*—Hybrid tea.

*Flower*

(Observations made from specimens grown in a greenhouse at Newark, New York, U.S.A., in the early afternoon during the latter part of April.)

Blooming habit: Recurrent—continuous.
Bud:
*Size.*—Large.
*Form.*—Pointed; ovoid; is not affected by wet or hot weather.
*Color.*—When sepals first divide—Ochraceous-Salmon, Plate 15, lightly overcast with Grenadine Pink, Plate 2. When petals begin to unfurl—Yellow Ocher, Plate 15. When half-blown: inside of petals—Pale Orange-Yellow, Plate 3, with outer edges of petals lightly overcast with Orange-Pink, Plate 2; reverse of petals—Baryta Yellow, Plate 4, with outer edges of the flower petals lightly overcast with Orange-Buff, Plate 3.
*Sepals.*—Branched; curl back when petals begin to unfurl. Color: inside—Pale Fluorite Green, Plate 32; outside—Oil Green, Plate 5.
*Calyx.*—Color—Oil Green, Plate 5. Size—large. Aspect—smooth. Odor when rubbed—none.
*Peduncle.*—Length — long. Aspect — prickly. Strength—erect; heavy. Color—Oil Green, Plate 5.
*Opening.*—Opens up well; is not affected by adverse weather conditions.
Bloom:
*Size.*—Very large. Average size when fully expanded—from 5½ to 6 inches.
*Borne.*—Singly.
*Stems.*—Long and strong.
*Form (when first open).*—High center. Permanence—retains its form to the end, but outer petals curl quill fashion like a cactus dahlia.
*Petalage.*—Very double (many petals and stamens hidden). Number of petals under normal conditions—from 55 to 60.
*Color.*—Center of flower—Light Salmon Orange, Plate 2. Outer petals—Pale Orange-Yellow, Plate 3, with lower half of petals overcast with Empire Yellow, Plate 4. Base of petals (aiglet)—Lemon Chrome, Plate 4. Inside of petals—Capucine Buff, Plate 3, lightly overcast with Orange-Pink, Plate 2, and with the lower half of the petals lightly overcast with Empire Yellow, Plate 4. Reverse of petals—Pale Yellow Orange, Plate 3, with lower half of the petals lightly overcast with Empire Yellow, Plate 4. General tonality from a distance—Capucine Buff, Plate 3, lightly overcast with Orange-Pink, Plate 2.
*Discoloration.*—General tonality at end of first day—Capucine Buff, Plate 3, lightly overcast with Orange-Pink, Plate 2. Second day—Capucine Buff, Plate 3, lightly overcast with Orange-Pink, Plate 2. Third day—Capucine Buff, Plate 3, lightly overcast with pale Orange-Yellow, Plate 3.
Petals:
*Texture.*—Leathery; is not affected by wet or hot weather.
*Appearance.*—Inside—satiny. Outside—shiny.
*Form.*—Oval.
*Arrangement.*—Informal (with "rags" in center).
*Petaloids in center.*—Many; large.
*Persistence.*—Drop off cleanly.
*Fragrance.*—Strong. Nature—tea (average hybrid tea scent).
*Lasting quality.*—On the plant—very long. As cut flower—very long.

*Genital organs*

Stamens, anthers: Large; many; mixed with petaloids. Color—Capucine Yellow, Plate 3.
Stamens, filaments (threads): Long. Color—Light Cadmium, Plate 4.
Pollen: Color—Pale Yellow-Orange, Plate 3.
Styles: Bunched; even; short; thin.
Stigmas: Color—Baryta Yellow, Plate 4.
Ovaries: All enclosed in calyx.
Hips: None.
Seeds: None.

*Plant*

Form: Bush.
Growth: Vigorous; upright.
Foliage: Compound of 3 to 7 leaflets.
*Size.*—Large.
*Quantity.*—Abundant.
*Color.*—New foliage: upper side—Yellowish Oil Green, Plate 5, with outer edges of leaves and serrations Oxblood Red, Plate 1; under side—Oxblood Red, Plate 1, with center of leaves Oil Green, Plate 5. Old foliage: upper side—Deep Dull Yellow-Green (2), Plate 17; under side—Chromium Green, Plate 32.
*Shape.*—Oval pointed.
*Texture.*—Upper side—leathery and glossy. Under side—smooth.
*Ribs and veins.*—Prominent.
*Edge.*—Serrated (saw-toothed).
*Serration.*—Both double and single; sharp.
*Leaf stem.*—Color—Biscay Green, Plate 17. Under side—prickly.
*Stipules.*—Long; bearded.
Wood:
*New wood.*—Color—Biscay Green, Plate 17. Bark—smooth.

*Old wood.*—Color—Cedar Green, Plate 6. Bark—smooth.
Thorns:
*Thorns.*—Quantity: on main stalks from base—many; on laterals from stalk—many. Form—broad base; long; straight. Color (when young)—Terra Cotta, Plate 28. Position—irregular.
*Prickles.*—Quantity: on main stalks—none; on laterals—none.
*Short needles.*—Quantity: on main stalks—none; on laterals—none.

I claim:

A new and distinct variety of rose plant of the hybrid tea class, substantially as herein shown and described, characterized particularly as to novelty by the unique combination of a free blooming habit and attendant suitability for greenhouse cut-flower production, strong flower stems, a distinctive Capucine Buff, lightly overcast with Orange-Pink general color tonality of the flowers, and a substantially uniform and prolonged flower color retention from beginning to end.

No references cited.